(12) United States Patent
Kurakami et al.

(10) Patent No.: US 9,751,822 B2
(45) Date of Patent: Sep. 5, 2017

(54) METHOD FOR PRODUCING UNSATURATED CARBOXYLIC ACID AND SUPPORTED CATALYST

(71) Applicant: Nippon Kayaku Kabushiki Kaisha, Tokyo (JP)

(72) Inventors: Tatsuhiko Kurakami, Yamaguchi (JP); Hideomi Sakai, Yamaguchi (JP); Toru Toki, Yamaguchi (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/027,351

(22) PCT Filed: Oct. 7, 2014

(86) PCT No.: PCT/JP2014/076818
§ 371 (c)(1),
(2) Date: Apr. 5, 2016

(87) PCT Pub. No.: WO2015/053269
PCT Pub. Date: Apr. 16, 2015

(65) Prior Publication Data
US 2016/0244393 A1    Aug. 25, 2016

(30) Foreign Application Priority Data

Oct. 10, 2013  (JP) ................................. 2013-212622

(51) Int. Cl.
| | |
|---|---|
| *C07C 51/25* | (2006.01) |
| *C07C 51/215* | (2006.01) |
| *C07C 51/235* | (2006.01) |
| *B01J 31/36* | (2006.01) |
| *B01J 37/08* | (2006.01) |
| *B01J 23/00* | (2006.01) |
| *B01J 23/888* | (2006.01) |
| *B01J 35/10* | (2006.01) |
| *B01J 37/00* | (2006.01) |
| *B01J 27/199* | (2006.01) |
| *B01J 27/24* | (2006.01) |

(52) U.S. Cl.
CPC ........... *C07C 51/252* (2013.01); *B01J 23/002* (2013.01); *B01J 23/8885* (2013.01); *B01J 27/199* (2013.01); *B01J 27/24* (2013.01); *B01J 31/36* (2013.01); *B01J 35/1009* (2013.01); *B01J 35/1014* (2013.01); *B01J 35/1038* (2013.01); *B01J 35/1042* (2013.01); *B01J 37/0036* (2013.01); *B01J 37/0045* (2013.01); *B01J 37/088* (2013.01); *C07C 51/215* (2013.01); *C07C 51/235* (2013.01); *B01J 2523/00* (2013.01)

(58) Field of Classification Search
CPC .... B01J 23/002; B01J 23/8885; B01J 27/199; B01J 27/24; B01J 31/36; B01J 35/1009; B01J 35/1014; B01J 35/1038; B01J 35/1042; B01J 37/0036; B01J 37/0045; B01J 37/088; C07C 51/215; C07C 51/235; C07C 51/252
See application file for complete search history.

(56) References Cited

U.S. PATENT DOCUMENTS

| | | | | |
|---|---|---|---|---|
| 5,716,895 | A | * | 2/1998 | Sugi ......................... B01J 38/74 502/22 |
| 5,959,143 | A | * | 9/1999 | Sugi ........................ B01J 23/002 502/302 |
| 6,028,220 | A | | 2/2000 | Wada et al. |
| 6,777,369 | B1 | | 8/2004 | Kuroda et al. |
| 2003/0109381 | A1 | | 6/2003 | Ohishi et al. |
| 2005/0215818 | A1 | | 9/2005 | Yunoki et al. |
| 2009/0234158 | A1 | | 9/2009 | Sudo et al. |
| 2011/0144406 | A1 | | 6/2011 | Masatsugu et al. |
| 2012/0065427 | A1 | | 3/2012 | Sudo et al. |
| 2015/0126774 | A1 | | 5/2015 | Hiraoka et al. |

FOREIGN PATENT DOCUMENTS

| | | |
|---|---|---|
| CN | 1351517 A | 5/2002 |
| CN | 1089081 C | 8/2002 |
| CN | 100345631 C | 10/2007 |
| EP | 2436443 A1 | 4/2012 |
| EP | 2842625 A1 | 3/2015 |
| EP | 2842626 A1 | 3/2015 |
| JP | 3775872 B2 | 5/2006 |

(Continued)

OTHER PUBLICATIONS

Chinese communication, with English translation, dated Oct. 21, 2016 in corresponding Chinese patent application No. 201480055832.1.
International Search Report and Written Opinion mailed Jan. 6, 2015 in corresponding PCT application No. PCT/JP2014/076818.
Sommer et al., "Auslegung von Granulierteller and Granuliertrommel," Chemie Ingenieur Technik, vol. 50, No. 7, Jan. 1, 1978, pp. 518-524.
European communication dated Jun. 7, 2017 in corresponding European patent application No. 14852394.7.

(Continued)

*Primary Examiner* — Paul A Zucker
*Assistant Examiner* — Mark Luderer
(74) *Attorney, Agent, or Firm* — Neilds, Lemack & Frame, LLC

(57) ABSTRACT

The present invention relates to a method for producing an unsaturated carboxylic acid using a catalyst having both a high catalytic performance and a high mechanical strength, and in the method, a supported catalyst obtained by feeding a liquid binder component and a catalytic active component containing molybdenum and vanadium and/or a precursor thereof into a rolling granulator and conducting granulation at a relative centrifugal acceleration of 0.5 G or more and 30 G or less is used.

6 Claims, No Drawings

(56) References Cited

FOREIGN PATENT DOCUMENTS

| JP | 3883755 B2 | 2/2007 |
|---|---|---|
| JP | 4437967 B2 | 3/2010 |
| JP | 4756890 B2 | 8/2011 |
| JP | 2012-110806 A | 6/2012 |
| JP | 2012-148202 A | 8/2012 |
| JP | 5130562 B2 | 1/2013 |
| WO | 2010/021397 A1 | 2/2010 |
| WO | 2013/161703 A1 | 10/2013 |

OTHER PUBLICATIONS

Chinese communication, with English translation, dated Jun. 28, 2017 in corresponding Chinese patent application No. 01480055832.1.

* cited by examiner

METHOD FOR PRODUCING UNSATURATED CARBOXYLIC ACID AND SUPPORTED CATALYST

TECHNICAL FIELD

The present invention relates to a method for producing an unsaturated carboxylic acid and a supported catalyst.

BACKGROUND ART

The shape of a catalyst which is used for a gas-solid catalytic reaction using a fixed bed reactor is chosen according to its application, and catalysts having a ring shape, a cylinder shape, a tablet shape, a honeycomb shape, a trefoil shape, a quatrefoil shape, and a spherical shape are frequently used. The spherical catalyst is widely used in view of the fact that it is easy to uniformly fill the catalyst in a large number of reaction tubes as well as from the standpoint of easiness in a work of filling the catalyst in the reaction tubes and a work of extracting the catalyst after the use from the reaction tubes. The supporting is widely used on an industrial scale as a method of increasing an external surface area of the catalyst and a method of solidifying an active component. As for a production method of a spherical supported catalyst, Patent Document 1 discloses a production method of a catalyst for producing acrolein and/or acrylic acid from propylene; Patent Document 2 discloses a production method of a catalyst for producing acrylic acid from acrolein; Patent Document 3 discloses a production method of a catalyst for producing methacrolein and/or methacrylic acid from isobutylene and/or tertiary butanol; and Patent Document 4 discloses a production method of a catalyst for producing methacrylic acid from methacrolein.

BACKGROUND ART DOCUMENT

Patent Document

Patent Document 1: Japanese Patent No. 375872
Patent Document 2: Japanese Patent No. 3883755
Patent Document 3: Japanese Patent No. 5130562
Patent Document 4: Japanese Patent No. 4756890
Patent Document 5: Japanese Patent No. 4437967

SUMMARY OF INVENTION

Problem that Invention is to Solve

In Patent Documents 1 to 4, a granulation method by a rolling granulation method is disclosed as the method of producing a spherical supported catalyst. Specifically, the spherical supported catalyst is produced by charging a rolling granulation apparatus with a spherical carrier necessary for obtaining a desired catalyst particle diameter and sprinkling a liquid serving as a binder and a catalytic active component and/or a precursor thereof over the carrier while rotating a bottom plate.

In addition, Patent Document 5 describes an example in which in producing a catalyst for acrylic acid production adopting a rolling granulation method, shaping is carried out in a state of inclining a rotary tray at 30° against the horizontal plane while rotating at 15 rpm. However, since Patent Document 5 does not describe the size of an instrument to be used, its relative centrifugal acceleration is unclear.

The catalysts produced by the above-described techniques are widely used on an industrial scale, and slight improvement of reaction yield, decrease of reaction temperature, and improvement of mechanical strength bring about extremely large economic effects, and hence, improvements of the catalysts are eagerly demanded.

Means for Solving Problem

According to studies made by the present inventors, it has been found to produce an unsaturated carboxylic acid using a catalyst which is produced by adjusting a diameter of a rolling granulator in a granulation step of a supported catalyst and a revolution rate of a bottom plate to give a specified relative centrifugal acceleration, thereby bringing about both high catalytic performance and high mechanical strength, leading to accomplishment of the present invention.

Specifically, the present invention is concerned with:
(1) A method for producing an unsaturated carboxylic acid, comprising:
using a supported catalyst obtained by feeding a liquid binder component and a catalytic active component containing molybdenum and vanadium and/or a precursor thereof into a rolling granulator and conducting granulation at a relative centrifugal acceleration of 0.5 G or more and 30 G or less;
(2) The method for producing an unsaturated carboxylic acid as described in (1) above,
wherein the catalytic active component and/or the precursor thereof of the supported catalyst contains molybdenum, vanadium and copper;
(3) The method for producing an unsaturated carboxylic acid as described in (1) above,
wherein the catalytic active component and/or the precursor thereof of the supported catalyst contains molybdenum, vanadium and phosphorus;
(4) A supported catalyst, which is obtained by feeding a liquid binder component and a catalytic active component containing molybdenum and vanadium and/or a precursor thereof into a rolling granulator and conducting granulation at a relative centrifugal acceleration of 0.5 G or more and 30 G or less;
(5) The supported catalyst as described in (4) above,
wherein the catalytic active component and/or the precursor thereof contains molybdenum, vanadium and copper; and
(6) The supported catalyst as described in (4) above,
wherein the catalytic active component and/or the precursor thereof contains molybdenum, vanadium and phosphorus.

Effects of Invention

According to the present invention, it is possible to produce an unsaturated carboxylic acid using a supported catalyst having both thorough mechanical strength and catalytic performance.

MODE FOR CARRYING OUT INVENTION

Next, preferred embodiments regarding the production of an unsaturated carboxylic acid in carrying out the present invention are described while referring to a production method of a catalyst for producing acrylic acid by partially oxidizing acrolein in the presence of molecular oxygen and a production method of acrylic acid using the same as examples.

The catalyst which is used for the production method of acrylic acid of the present invention (hereinafter also referred to as "catalyst of the present invention") is not particularly limited with respect to other metal components so long as it contains molybdenum and vanadium as catalytic active elements. A formulation of a composite metal oxide which is preferred as an active component of the catalyst for acrylic acid production is, for example, represented by the following formula.

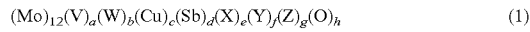

$$(Mo)_{12}(V)_a(W)_b(Cu)_c(Sb)_d(X)_e(Y)_f(Z)_g(O)_h \qquad (1)$$

(In the formula, Mo, V, W, Cu, Sb and O represent molybdenum, vanadium, tungsten, copper, antimony and oxygen, respectively; X represents at least one element selected from the group consisting of an alkali metal and thallium; Y represents at least one element selected from the group consisting of magnesium, calcium, strontium, barium and zinc; Z represents at least one element selected from the group consisting of niobium, cerium, tin, chromium, manganese, iron, cobalt, samarium, germanium, titanium and arsenic; and a, b, c, d, e, f, g, and h represent atomic ratios of the respective elements, in which a is ($0<a \leq 10$), b is ($0 \leq b \leq 10$), c is ($0<c \leq 6$), d is ($0 \leq d \leq 10$), e is ($0 \leq e \leq 0.5$), f is ($0 \leq f \leq 1$) and g is ($0 \leq g<6$) relative to 12 of the molybdenum atom, and h is a number of oxygen atoms necessary for satisfying valences of the above-described respective components.)

In the above-described catalyst of the present invention, it is preferred that copper is an essential component in addition to molybdenum and vanadium, and in that case, the formulation represented by the foregoing formula (1) is preferred.

The catalyst of the present invention can be obtained by calcining a powder obtained by drying a mixture of a compound containing catalytic active elements and water and then shaping the mixture by a rolling granulation method. Preferred embodiments are hereunder described for every step.

Step (a): Preparation

Though a raw material which is used for preparing the catalytic active component is not particularly limited, generally used ammonium salts, nitrates, sulfates, acetates, oxides, and chlorides, and so on are used. As for specific examples of these compounds, molybdenum trioxide, molybdic acid or salts thereof, and the like are exemplified as a molybdenum-containing compound; vanadium pentoxide, vanadyl sulfate, vanadic acid or salts thereof, and the like are exemplified as a vanadium-containing compound; copper oxide, copper sulfate, copper nitrate, copper acetate, copper molybdate, and the like are exemplified as a copper-containing compound; and antimony trioxide, antimony pentoxide, antimony acetate, antimony trichloride, and the like are exemplified as an antimony-containing compound. In addition, tungstic acid or salts thereof, and the like are exemplified as a tungsten-containing compound. In preparing the catalyst of the present invention, first of all, the above-described catalytic active element-containing compound and water are mixed to prepare an aqueous solution or an aqueous dispersion. Such an aqueous solution or aqueous dispersion is hereunder collectively referred to simply as "slurry solution" unless otherwise indicated. In the present invention, the solvent for forming the slurry solution is preferably water. A content proportion of each of the catalytic active element compounds in the slurry solution is not particularly limited, and it has only to fall within the atomic ratio of the foregoing formula (1). On the occasion of adding the respective component raw materials, the each component raw material is preferably dissolved or dispersed in water and then added; however, an amount of use of water to be used on that occasion is not particularly limited so long as it is an amount such that the whole of the used compounds can be completely dissolved (or uniformly mixed). However, the amount of water to be used is properly determined taking into consideration a drying step or a temperature as described below, or the like, and in general, it is 200 to 2,000 parts by weight based on 100 parts by weight of a total weight of the compounds. When the amount of water is too small, the compounds cannot be completely dissolved (or uniformly mixed). In addition, when the amount of water is too large, there is caused an economic problem that the energy cost of the drying step increases, or a problem that the drying becomes insufficient.

Step (b): Drying

Subsequently, the uniform slurry solution obtained above is dried. A drying method is not particularly limited so long as it is a method capable of drying the slurry solution to obtain a powder in which the component elements become uniform as a whole, and examples thereof include drum drying, freeze drying, spray drying, and the like. Among these, in the present invention, spray drying is preferred for the reason that drying can be achieved within a short period of time from the slurry solution state to the powdered state. Though a drying temperature varies with a concentration or a liquid sending speed of the slurry solution, or the like, the temperature at an outlet of a dryer is approximately 85 to 130° C. In addition, it is preferred to carry out the drying in such a manner that an average particle diameter of the dry powder obtained on this occasion is 20 to 60 μm.

Step (c): Preliminary Calcination/Pulverization

Subsequently, if desired, the dry powder obtained above is calcined at 200 to 600° C., and preferably 300 to 450° C. for 1 to 15 hours, and preferably 3 to 8 hours, and if desired, the powder after calcination is pulverized to obtain a preliminarily calcined granule.

Step (d): Shaping

The catalyst of the present invention is one produced by coating and supporting the granule prepared through the above-described steps on a spherical carrier having a diameter of 2.5 to 10 mm, such as silicon carbide, alumina, mullite, alundum, etc., by using a liquid binder component by a rolling granulation method or the like at a centrifugal acceleration of 0.5 G to 30 G. The rolling granulation method is a method in which, for example, in an apparatus having a flat or irregular disk in a bottom portion of a fixed container, the carrier within the container is vigorously agitated by repeating rotation movement and revolution movement by rotating the disk at a high speed, and a mixture of the liquid binder and the preliminarily calcined granule, and optionally a shaping auxiliary agent and a strength improver is added therein, thereby coating the resulting mixture on the carrier. At this time, by regulating the centrifugal acceleration to 0.5 G to 30 G, it is possible to produce a catalyst having both catalytic performance and mechanical strength. On the occasion of granulation, when the relative centrifugal acceleration is small, the mechanical strength is weak so that the catalyst component is exfoliated by a filling work in reaction tubes, and hence, a supporting rate of the active component becomes non-uniform, or a pressure loss is increased by the exfoliated powder. Thus, the resulting catalyst is not suitable for practical use. In addition, when the relative centrifugal acceleration is large, the catalytic performance tends to be lowered. When the relative centrifugal acceleration is more than 30 G, there may be the case where exfoliation of the catalytic active component or the like is generated during the granulation step, and hence, such is not preferred. The relative centrifugal acceleration can be calculated according to the following formula.

Relative centrifugal acceleration (G)=11.18×[radius of bottom plate (m)]×[revolution rate of bottom plate (rpm)]$^2$×10$^{-8}$ (2)

Though an attrition resistance of the actually used catalyst is preferably smaller, so long as it is 1.0% or less, the catalyst can be used without any problem for practical use, and there is not perceived a difference in use. When the attrition resistance is in the range of from 1.0 to 2.0%, the catalytic component is slightly exfoliated by a work of filling the catalyst in reaction tubes or the like, but there is no problem in actually carrying out the reaction.

In the present invention, the matter that the catalyst is weak in mechanical strength so that it is not suitable for practical use means a catalyst whose attrition resistance is more than 2%.

There may be arbitrarily adopted a method of adding the whole amount of the liquid binder by properly combining a method of previously mixing the liquid binder with the above-described mixture; a method of adding the liquid binder at the same time of adding the mixture in a fixed container; a method of adding the liquid binder after adding the mixture; a method of adding the liquid binder before adding the mixture; a method of dividing each of the mixture and the liquid binder and adding them simultaneously or alternately; and the like. Among these, in the method of dividing each of the mixture and the liquid binder and adding them alternately, it is preferred to carry out the addition of the liquid binder while adjusting its addition rate by using an auto feeder or the like in such a manner that, for example, a prescribed amount of the liquid binder is supported on the carrier without causing attachment of the mixture onto the wall of the fixed container, or coagulation of the mixtures each other.

Examples of the liquid binder include water, ethanol, polyvinyl alcohol as a polymer-based binder, a silica sol aqueous solution as an inorganic binder, and the like. Of these, alcohols, such as diols or diols, e.g., ethylene glycol, glycerin, etc., are preferred, and glycerin is especially preferred. Though the alcohol may be used as it is, it is effective to use the alcohol as an aqueous solution having a concentration of 10% by weight or more from the standpoint of obtaining a high-performance catalyst. An amount of use of such a liquid binder is generally 10 to 50 parts by weight based on 100 parts by weight of the preliminarily calcined granule.

Specific examples of the carrier which can be used include spherical carriers having a diameter of 2.5 to 10 mm, such as silicon carbide, alumina, mullite, alundum, etc., and the like. Among these carriers, it is preferred to use a carrier having a porosity of 30 to 50%/0, a coefficient of water absorption of 10 to 30%, and a cumulative specific surface area of 0.1 to 50 m$^2$/g and a cumulative pore volume of 0.05 to 2 ml/g, as measured by a mercury porosimeter. The preliminarily calcined granule to be added to the carrier is used by adjusting a ratio of the preliminarily calcined granule to a total of the preliminarily calcined granule and the carrier of generally 10 to 75% by weight, and preferably 15 to 50% by weight.

Step (e): Full-Scale Calcination

The thus obtained shaped article after shaping is again calcined (subjected to full-scale calcination), whereby the catalyst can be obtained. A full-scale calcination temperature is generally 250 to 500° C., and preferably 300 to 450° C., and a full-scale calcination time is generally 1 to 50 hours, and preferably 3 to 8 hours.

A production method of acrylic acid by the thus obtained shaped catalyst may be either a simple circulation method or a reaction raw material recycle method, and it can be carried out under known conditions. For example, the reaction is carried out by introducing a mixed gas composed of 2 to 10% by volume, and preferably 3 to 9% by volume of acrolein as a starting raw material, 2 to 12% by volume, and preferably 3 to 10% by volume of molecular oxygen, 0 to 40% by volume, and preferably 5 to 35% by volume of a water vapor, 28 to 93% by volume, and 35 to 86% by volume of an inert gas (e.g., nitrogen, carbon dioxide, etc.), and the like onto the above-described catalyst in a space velocity (=(raw material gas flow rate)/(apparent volume of the filled catalyst) of 500 to 3,000/hr at 200 to 400° C. under a pressure of 0 to 200 kPaG in terms of a gauge pressure. It is to be noted that a gas obtained by oxidizing propylene by a known method may be used as the above-described mixed gas. In this case, unreacted propylene or other by-product may be coexistent. In addition, a gas obtained by dehydrating glycerin by a known method may also be used.

Next, preferred embodiments in carrying out the present invention are described while referring to a production method of a catalyst for producing methacrylic acid by partially oxidizing methacrolein, isobutyl aldehyde, or isobutyric acid in the presence of molecular oxygen and a production method of methacrylic acid using the same as examples.

The catalyst of the present invention is not particularly limited with respect to other metal components so long as it contains molybdenum and vanadium as catalytic active elements. A formulation of a preferred composite metal oxide is, for example, represented by the following formula.

$$Mo_{10}V_aP_b(NH_4)_cX_dY_eO_f \quad (3)$$

In the foregoing formula (3), Mo represents molybdenum; V represents vanadium; P represents phosphorus; (NH$_4$) represents an ammonium group; X represents at least one element selected from K, Rb and Cs; Y represents at least one element selected from the group consisting of Sb, As, Cu, Ag, Mg, Zn, Al, B, Ge, Sn, Pb, Ti, Zr, Cr, Re, Bi, W, Fe, Co, Ni, Ce and Th; and a to e represent atomic ratios of the respective elements, in which a is (0.1≤a≤6.0), and preferably (0.3≤a≤2.0), b is (0.5≤b≤6.0), and preferably (0.7≤b≤2.0), c is (0≤c≤10.0), and preferably (0≤c≤5), d is (0≤d≤3.0), and preferably (0≤d≤1.5), e is (0≤e≤3), and preferably (0.01≤e≤0.5), and f is a numerical value determined by oxidized states of the respective elements other than O and atomic ratios thereof.

In the above-described catalyst of the present invention, it is preferred that phosphorus is an essential component in addition to molybdenum and vanadium, and in that case, the formulation represented by the foregoing formula (3) is preferred.

Furthermore, in the foregoing formula (3), the X component is preferably Cs, and the Y component is preferably at least one element selected from the group consisting of Sb, As and Cu.

Preferred embodiments are hereunder described for every step.

Step (a): Preparation

First of all, examples of the active component-containing compound which is used for the catalyst preparation include chlorides, sulfates, nitrates, oxides, acetates, and the like of the active component elements. More specific examples of the preferred compound include nitrates, such as potassium nitrate, cobalt nitrate, etc.; oxides, such as molybdenum oxide, vanadium pentoxide, antimony trioxide, cerium oxide, zinc oxide, germanium oxide, etc.; acids (or salts thereof), such as orthophosphoric acid, phosphoric acid, boric acid, aluminum phosphate, 12-tungstophosphoric acid, etc.; and the like. These active component-containing compounds may be used solely, or two or more kinds thereof may be mixed and then used. The slurry solution can be obtained by uniformly mixing the each active component-containing compound and water. An amount of use of water in the slurry solution is not particularly limited so long as it is an amount such that the whole of the used compounds can be completely dissolved or uniformly mixed. The amount of use of water has only to be properly determined taking into consideration a drying method or a drying condition. In general, the amount of use of water is about 200 to 2,000 parts by mass based on 100 parts by mass of a total mass of the compounds for slurry solution preparation. Though the amount of water may be large, when it is excessively large, there are frequently such demerits that the energy cost in the drying step increases; and that the case where drying cannot be completely achieved is possibly generated.

As for a temperature on the occasion of preparing the slurry solution, it is preferred to carry out heating to a temperature at which the compound containing molybdenum, phosphorus, vanadium, and optionally other metal element can be thoroughly dissolved.

Step (b): Addition of X Component in the Preparation

In the case of adding the X component in the step (b), cesium is preferred, and a cesium-containing compound as well as cesium hydroxide or a cesium weak acid salt, such as cesium acetate, cesium carbonate, etc., is preferred.

Step (c): Addition of Ammonium

In the case of adding an ammonium in the step (c), ammonium acetate or ammonium hydroxide is preferred as the ammonium compound to be used.

In the steps (b) and (c), it is preferred that a temperature of the slurry solution containing at least molybdenum, phosphorus, and vanadium is generally in the range of from about 0 to 35° C., and preferably from about 0 to 30° C. because the resulting catalyst tends to have high activity. In the case of adding the Y component, a step of addition is not particularly limited, and the Y component may be properly added during the steps (a) to (f). Examples of the raw material of the Y component include inorganic acids, chlorides, sulfates, nitrates, oxides, acetates, and the like of the component elements.

Step (d): Drying

A drying method in the step (d) is not particularly limited so long as it is a method in which the slurry solution can be completely dried, and the component elements become uniform as a whole, and examples thereof include drum drying, freeze drying, spray drying, evaporation to dryness, and the like. Among these, in the present invention, spray drying in which the slurry solution can be dried into a powder or a granule within a short period of time is especially preferred. Though a drying temperature of the spray drying varies with a concentration or a liquid sending speed of the slurry solution, or the like, the temperature at an outlet of a dryer is approximately 70 to 150° C. In addition, it is preferred to carry out the drying in such a manner that an average particle diameter of the dry powder of the slurry solution obtained on this occasion is 10 to 700 μm.

Step (e): Preliminary Calcination

In the step (e), the catalytic active component granule is preliminarily calcined as the need arises. In particular, in the catalyst containing the X component, there is a tendency that by carrying out the step (e), the moldability or mechanical strength is improved, and hence, it is preferred to carry out the step (e) in the catalyst containing the X component.

Step (f): Shaping

The shaping by the step (f) is carried out for the purpose of coating and supporting the resultant on a spherical carrier having a diameter of 2.5 to 10 mm, such as silicon carbide, alumina, mullite, alundum, etc., by a rolling granulation method or the like at a centrifugal acceleration of 0.5 G to 30 G. This method is a method in which, for example, in an apparatus having a flat or irregular disk in a bottom portion of a fixed container, the carrier within the container is vigorously agitated by repeating rotation movement and revolution movement by rotating the disk at a high speed, and a coating mixture of the binder and the dry powder, and optionally other additives, for example, a shaping auxiliary agent and a strength improver are added therein, thereby coating the resulting mixture on the carrier. At this time, by regulating the centrifugal acceleration to 0.5 G to 30 G, it is possible to produce a catalyst having both catalytic performance and mechanical strength. The relative centrifugal acceleration can be calculated according to the foregoing formula (2).

On the occasion of the preparation, when the centrifugal acceleration is small, the resulting catalyst is weak in mechanical strength and is not suitable for practical use. When the centrifugal acceleration is large, it is difficult to achieve shaping to such extent that the catalyst is usable, and furthermore, the catalytic performance tends to be lowered.

In the present invention, the matter that the catalyst is weak in mechanical strength so that it is not suitable for practical use means a catalyst whose attrition resistance is more than 2%.

As for an addition method of the liquid binder, there may be arbitrarily adopted (1) and (2) a method of adding the liquid binder at the same time of adding the coating mixture in a fixed container; (3) a method of adding the liquid binder after adding the coating mixture in a fixed container; (4) a method of adding the liquid binder before adding the coating mixture in a fixed container; (5) a method of dividing each of the coating mixture and the liquid binder and adding the whole of the liquid binder by properly combining the methods (2) to (4); and the like. Among these, in the method (5), it is preferred to carry out the addition of the liquid binder while adjusting its addition rate by using an auto feeder or the like in such a manner that, for example, a prescribed amount of the liquid binder is supported on the carrier without causing attachment of the coating mixture onto the wall of the fixed container, or coagulation of the coating mixtures each other. The liquid binder is not particularly limited so long as it is at least one member selected from the group consisting of water and organic compounds having a boiling point of 150° C. or lower at 1 atm or less. Specific examples of the binder other than water include an alcohol, such as methanol, ethanol, propanol, butanol, etc., and preferably an alcohol having 1 to 4 carbon atoms; an ether, such as ethyl ether, butyl ether, dioxane, etc.; an ester, such as ethyl acetate, butyl acetate, etc.; a ketone, such as acetone, methyl ethyl ketone, etc.; and an aqueous solution thereof, with ethanol being especially preferred. In the case of using ethanol as the binder, it is preferred to mix it with water in a ratio of ethanol to water of 10/0 to 0/10 (mass ratio), and the ratio is more preferably 9/1 to 1/9 (mass ratio). An amount of use of such a liquid binder is generally 2 to 60 parts by mass, and preferably 10) to 50 parts by mass based on 100 parts by mass of the coating mixture.

Specific examples of the carrier which can be used include spherical carriers having a diameter of 1 to 15 mm, and preferably 2.5 to 10 mm, such as silicon carbide, alumina, silica alumina, mullite, alundum, etc., and the like. In general, those carriers having a porosity of 10 to 70% are used. It is preferred to use a carrier having a cumulative specific surface area of 0.1 to 50 $m^2/g$ and a cumulative pore volume of 0.05 to 2 ml/g, as measured by a mercury porosimeter. As for a proportion of the carrier and the coating mixture, the amount is normally regulated such that a ratio of {(coating mixture)/[(coating mixture)+(carrier)]× 100} is 10 to 75% by mass, and preferably 15 to 60% by mass. In the foregoing, it is to be noted that examples of the shaping auxiliary agent which is used, if desired include silica gel, diatomaceous earth, an alumina powder, and the like. An amount of use of the shaping auxiliary agent is generally 1 to 60 parts by mass based on 100 parts by mass of the dry powder. In addition, what an inorganic fiber (for example, a ceramic fiber, a whisker, etc.) which is inactive with the catalytic active component and the reaction gas is used as the strength improver as the need further arises is useful for improving the mechanical strength of the catalyst, and a glass fiber is especially preferred. An amount of use of such a fiber is generally 1 to 30 parts by mass based on 100 parts by mass of the dry powder.

Step (g): Full-Scale Calcination

Though the coated catalyst obtained in the step (f) can be directly provided as a catalyst for the catalytic gas phase oxidation reaction, it is also possible to subject the coated catalyst obtained in the step (f) to calcination (full-scale calcination) for the purpose of removing the binder, the shaping auxiliary agent, the strength improver, and the like as added in the shaping step. When the full-scale calcination is carried out, there may be the case where the catalytic activity is improved, and hence, such is preferred. In this case, a calcination temperature is generally 100 to 450° C., preferably 250° C. to 420° C., more preferably 250 to 400° C., and still more preferably 300 to 400° C. A calcination time is 1 to 20 hours. It is to be noted that though the calcination is generally carried out under an air atmosphere, it may also be carried out under an inert gas atmosphere, such as nitrogen, or under a reducing gas atmosphere, such as ethanol. After the calcination under an inert gas or reducing gas atmosphere, calcination may further be carried out under an air atmosphere as the need arises. A proportion of the active component relative to the whole of the thus obtained coated catalyst is preferably 10 to 60% by mass.

The catalyst which has been prepared in the above-described steps is used for the production of methacrylic acid by means of gas phase catalytic oxidation of methacrolein, tertiary butyl alcohol, isobutyl aldehyde, or isobutyric acid. The gas phase catalytic reaction using methacrolein as a raw material which is the most preferred in using the catalyst of the present invention is hereunder described. Molecular oxygen or a molecular oxygen-containing gas is used for the gas phase catalytic oxidation reaction. A proportion of use of molecular oxygen to methacrolein is preferably in the range of from 0.5 to 20, and especially preferably in the range of from 1 to 10 in terms of a molar ratio. For the purpose of allowing the reaction to smoothly proceed, it is preferred to add water in an amount ranging from 1 to 20 relative to methacrolein in terms of a molar ratio in the raw material gas. The raw material gas may contain, in addition to oxygen and optionally water (generally contained as a water vapor), a gas which is inert to the reaction, such as nitrogen, carbon dioxide, a saturated hydrocarbon, etc., and the like. In addition, as for the methacrolein, a gas obtained by oxidation of isobutylene, tertiary butanol, and methyl tertiary butyl ether may be fed as it is. A reaction temperature in the gas phase catalytic oxidation reaction is generally 200 to 400° C., and preferably 260 to 360° C., and a feed amount of the raw material gas is generally 100 to 6,000 $hr^{-1}$, and preferably 300 to 3,000 $hr^{-1}$ in terms of a space velocity (SV). In addition, though it is possible to carry out the gas phase catalytic oxidation reaction under an elevated pressure or a reduced pressure, in general, a pressure in the vicinity of atmospheric pressure is suitable.

EXAMPLES

Embodiments to be carried out by the present invention are hereunder described in detail by reference to specific examples. As a matter of course, it should not be construed that the present invention is limited to the following Examples so long as the gist of the present invention is not deviated.

It is to be noted that in the Examples and Comparative Examples, the term "parts" means a weight part. In addition, the acrolein yield and the acrylic acid yield are defined according to the following formulae (4) to (5).

Acrolein yield (mol %)=100×(molar number of produced acrolein)/(molar number of fed propylene) (4)

Acrylic acid yield (mol %)=100×(molar number of produced acrylic acid)/(molar number of fed propylene) (5)

In addition, the methacrolein conversion and the methacrylic acid yield are defined according to the following formulae (6) to (7).

Methacrolein conversion (mol %)=100×[(molar number of fed methacrolein)−(molar number of unreacted methacrolein)]/(molar number of fed methacrolein) (6)

Methacrylic acid yield (mol %)=100×(molar number of produced methacrylic acid)/(molar number of fed methacrolein) (7)

Example 1

In a mixing tank (A) equipped with an agitation motor, 600 parts of pure water at 95° C. and 16.26 parts of ammonium tungstate were added and agitated. Subsequently, 18.22 parts of ammonium metavanadate and 110 parts of ammonium molybdate were dissolved therein. Subsequently, 3.88 parts of antimony trioxide was added. In a mixing tank (B) charged with 96 parts of deionized water, 15.56 parts of copper sulfate was dissolved, and the resulting solution was added in the mixing tank (A) to obtain a slurry solution. The thus obtained slurry solution was dried by adjusting a liquid sending amount such that an outlet temperature of a spray dryer was about 100° C. The thus obtained granule was subjected to preliminary calcination under air circulation at 390° C. for 5 hours.

Subsequently, the preliminarily calcined granule was pulverized by a ball mill, to obtain a powder (hereinafter referred to as "preliminarily calcined powder"). 300 parts of an alundum carrier having a diameter of 4.5 mm was charged into a rolling granulator having a diameter of a bottom plate of 23 cm, and the bottom plate was rotated at 100 rpm, thereby regulating a centrifugal acceleration to 1.3 G. The above-obtained preliminarily calcined powder was supported at a supporting rate of 30% by weight while sprinkling 50 parts of a 20% by weight glycerin aqueous solution thereover. The resulting shaped article was calcined under air circulation at 390° C. for 5 hours, thereby obtaining a catalyst A1. An active component ratio of the catalyst A1 was $Mo_{12}V_3W_{1.2}Cu_{1.2}Sb_{0.5}$ when the ratio of molybdenum was defined as 12.

(Oxidation Reaction)

In, as a front stage reactor, a stainless steel-made reactor having an inner diameter of 28.4 mm and equipped with a jacket for fluidizing an alumina powder as a heating medium by air and a thermocouple for measuring a catalyst layer temperature in a tube axis, 68 mil of a catalyst containing, as major components, supported catalyst molybdenum, bismuth, and iron was filled, and a reaction bath temperature was set to 320° C.

A gas in which feed amounts of propylene, air and water had been set in a raw material molar ratio of propylene to oxygen to nitrogen to water of 1/1.7/6.4/3.0 was introduced into the oxidation reactor at a space velocity of 862 $h^{-1}$, thereby producing a reaction product gas containing acrolein. At this time, a rate of reaction of propylene was 97%.

In, as a rear stage reactor, a stainless steel-made reactor having an inner diameter of 28.4 mm and equipped with a jacket for fluidizing an alumina powder as a heating medium by air and a thermocouple for measuring a catalyst layer temperature in a tube axis, 68 ml of the catalyst A1 was filled, and a reaction bath temperature was set to 260° C. A gas prepared by mixing the whole amount of the reaction product gas from the front stage reactor with air whose flow rate had been adjusted such that a molar ratio of oxygen to propylene at an inlet of the front stage reactor was 0.5 was fed into the rear stage reactor.

After commencement of the reaction, when elapsing 20 hours, a quantitative analysis of the reaction product by means of gas chromatography was carried out to determine the acrolein yield and the acrylic acid yield at an outlet of the rear stage reactor. The results are shown in Table 1.

(Strength Measurement)

50.0 g of the catalyst A1 was charged into a cylindrical rotating machine having a radius of 14 cm, the machine being provided with one baffle plate in the inside thereof, and the machine was rotated at 23 rpm for 10 minutes. Thereafter, the exfoliated powder was removed by a sieve, the remaining amount on the sieve was measured, and an attrition resistance (%) was determined according to the following formula. The results are shown in Table 1.

Attrition resistance (%)=[50.0−(remaining amount)]/50.0×100

Example 2

A catalyst A2 was prepared in the same method as in Example 1, except that in Example 1, the revolution rate of the bottom plate of the rolling granulator was set to 180 rpm, thereby regulating the centrifugal acceleration to 4.2 G and the same evaluations as in Example 1 were carried out.

The oxidation reaction results and the strength measurement results of the catalyst A2 are shown in Table 1.

Example 3

A catalyst A3 was prepared in the same method as in Example 1, except that in Example 1, the revolution rate of the bottom plate of the rolling granulator was set to 330 rpm, thereby regulating the centrifugal acceleration to 14 (1 and the same evaluations as in Example 1 were carried out.

The oxidation reaction results and the strength measurement results of the catalyst A3 are shown in Table 1.

Example 4

A catalyst A4 was prepared in the same method as in Example 1, except that in Example 1, the revolution rate of the bottom plate of the rolling granulator was set to 400 rpm, thereby regulating the centrifugal acceleration to 21 G, and the same evaluations as in Example 1 were carried out.

The oxidation reaction results and the strength measurement results of the catalyst A4 are shown in Table 1.

Comparative Example 1

A catalyst B1 was prepared in the same method as in Example 1, except that in Example 1, the revolution rate of the bottom plate of the rolling granulator was set to 50 rpm, thereby regulating the centrifugal acceleration to 0.32 G, and the same evaluations as in Example 1 were attempted.

The attrition resistance of the catalyst B1 was 4.31% as shown in Table 1, and hence, the resulting catalyst did not have a strength suitable for practical use. For that reason, the oxidation reaction test was not carried out.

In the light of the above, when the centrifugal acceleration is too small, the produced catalyst is satisfactory with the supporting rate itself as designed and has a uniform shape on appearance. However, the attrition resistance is too large, and hence, due to a transportation work, a filling operation in reaction tubes, or the like, the exfoliation of the catalyst component is generated, and a lowering of activity, an increase of pressure loss, and so no are generated. The generated exfoliated powdered catalyst causes an increase of pressure within the reaction tubes, and hence, such is not preferred.

In addition, with respect to catalysts having an attrition resistance of more than 4%, even in the same shaping lot, the attrition resistance considerably varies depending upon every sample, and therefore, the reaction results are also changed. For these reasons, the oxidation reaction test was not carried out in Comparative Example 1.

Comparative Example 2

A catalyst B2 was prepared in the same method as in Example 1, except that in Example 1, the revolution rate of the bottom plate of the rolling granulator was set to 490 rpm, thereby regulating the centrifugal acceleration to 31 G and the same evaluations as in Example 1 were attempted.

The catalyst B2 did not become uniform in supporting because the exfoliation of the catalytic active component was generated during preparation and was judged to be a product which could not be adopted as a practically useful catalyst. Thus, the subsequent steps and the strength measurement and oxidation reaction test were not carried out.

In the light of the above, when the centrifugal acceleration is too large, the once supported catalytic active component is exfoliated into a plate-like form from the carrier, and the shape of the catalyst does not become a fixed shape. In addition, due to the generation of chipping, the supporting rate of the catalyst becomes smaller than the designed value. Furthermore, the exfoliation is not uniformly generated among catalysts within the same shaping lot, but the degree of exfoliation varies in every granule. Thus, the catalyst is never useful on an industrial scale. For these reasons, the strength measurement and oxidation reaction test were not carried out in Comparative Example 2.

TABLE 1

| Catalyst name | Relative centrifugal acceleration (G) | Attrition resistance (%) | Acrolein yield (mol %) | Acrylic acid yield (mol %) |
| --- | --- | --- | --- | --- |
| A1 | 1.3 | 0.46 | 0.65 | 87.5 |
| A2 | 4.2 | 0.52 | 0.51 | 87.2 |
| A3 | 14 | 0.97 | 0.45 | 87.2 |
| A4 | 21 | 1.95 | 0.49 | 87.2 |
| B1 | 0.32 | 4.31 | Not carried out | Not carried out |
| B2 | 31 | Not carried out | Not carried out | Not carried out |

Example 5

To 5,680 ml of pure water, 800 parts of molybdenum trioxide, 30.33 parts of vanadium pentoxide, and 76.87 parts of an 85% by mass orthophosphoric acid were added, and the contents were heated and agitated at 92° C. for 3 hours to obtain a reddish brown transparent solution. Subsequently, this solution was cooled to 0 to 20° C., to which was then gradually added 661.32 parts of a 9.1% by mass cesium hydroxide aqueous solution, and the contents were aged at 15 to 20° C. for 1 hour to obtain a yellow slurry solution. Subsequently, 196.86 parts of a 50.0% by mass ammonium acetate aqueous solution was gradually added to the slurry, and the resultant was further aged at 0 to 30° C. for 1 hour. Subsequently, 22.18 parts of cupric acetate was further added to the resulting slurry, and the contents were agitated and mixed until the cupric acetate was completely dissolved. Subsequently, this slurry was spray dried to obtain a catalytic active component solid. A formulation of the catalytic active component solid as determined from the charged amounts of the raw materials is $Mo_{10}V_{0.6}P_{1.1}Cs_{0.7}(NH_4)_{2.3}Cu_{0.3}$.

The resulting active component granule was calcined at 300° C. over 6 hours to obtain a preliminarily calcined powder.

200 parts of a spherical porous alumina carrier having a diameter of 4.5 mm and having a cumulative specific surface area of 1.1 m$^2$/g, and a cumulative pore volume of 0.21 m$^2$/g, measured by a mercury porosimeter was charged into a rolling granulator having a diameter of a bottom plate of 23 cm. By rotating the bottom plate at 75 rpm, the centrifugal acceleration was set to 0.72 G.

120 parts of the preliminarily calcined powder and 6.5 parts of a strength improver (glass fiber) were uniformly mixed and subjected to coating and shaping with about 30 parts of a 50% by mass ethanol aqueous solution as a liquid binder by a rolling granulation method. Subsequently, the resulting shaped product was calcined under air circulation at 380° C. over 5 hours, thereby obtaining a desired coated catalyst A5.

(Oxidation Reaction Test)

10.3 ml of the resulting catalyst A5 was filled in a stainless steel-made reaction tuber having an inner diameter of 18.4 mm, and an oxidation reaction of methacrolein was carried out by using a raw material gas (molar ratio: methacrolein to oxygen to water vapor to nitrogen=1/2/4/18.6) under conditions at a space velocity (SV) of 1,200 hr$^{-1}$ and a reaction bath temperature of 310° C. The reaction was continued at a reaction bath temperature of 310° C. for 3 hours. Subsequently, the reaction bath temperature was increased to 350° C., and the reaction was continued for 15 hours. The reaction bath temperature was decreased to 310° C., and a quantitative analysis of the reaction product was carried out by means of gas chromatography, thereby determining the reaction results. The obtained results are shown in Table 2.

(Strength Measurement)

50.0 g of the catalyst A5 was charged into a cylindrical rotating machine having a radius of 14 cm, the machine being provided with one baffle plate in the inside thereof, and the machine was rotated at 23 rpm for 10 minutes. Thereafter, the exfoliated powder was removed by a sieve, the remaining amount on the sieve was measured, and an attrition resistance (%) was determined according to the following formula. The results are shown in Table 2.

Attrition resistance (%)=[50.0−(remaining amount)]/50.0×100

Example 6

A catalyst A6 was prepared in the same method as in Example 5, except that in Example 5, the revolution rate of the bottom plate of the rolling granulator was set to 160 rpm, thereby regulating the centrifugal acceleration to 3.3 G and the same evaluations as in Example were carried out.

The oxidation reaction results and the strength measurement results of the catalyst A6 are shown in Table 2.

Example 7

A catalyst A7 was prepared in the same method as in Example 5, except that in Example 5, the revolution rate of the bottom plate of the rolling granulator was set to 200 rpm, thereby regulating the centrifugal acceleration to 5.1 G, and the same evaluations as in Example were carried out.

The oxidation reaction results and the strength measurement results of the catalyst A7 are shown in Table 2.

Example 8

A catalyst A8 was prepared in the same method as in Example 5, except that in Example 5, the revolution rate of the bottom plate of the rolling granulator was set to 280 rpm, thereby regulating the centrifugal acceleration to 10 G, and the same evaluations as in Example 5 were carried out.

The oxidation reaction results and the strength measurement results of the catalyst A8 are shown in Table 2.

Example 9

A catalyst A9 was prepared in the same method as in Example 5, except that in Example 5, the revolution rate of the bottom plate of the rolling granulator was set to 400 rpm, thereby regulating the centrifugal acceleration to 21 G, and the same evaluations as in Example 5 were carried out.

The oxidation reaction results and the strength measurement results of the catalyst A9 are shown in Table 2.

Comparative Example 3

A catalyst B3 was prepared in the same method as in Example 5, except that in Example 5, the revolution rate of the bottom plate was set to 50 rpm, thereby regulating the centrifugal acceleration to 0.32 G, and the same evaluations as in Example 5 were attempted.

The oxidation reaction results and the strength measurement results of the catalyst B3 are shown in Table 2.

Comparative Example 4

A catalyst B4 was prepared in the same method as in Example 5, except that in Example 5, the revolution rate of the bottom plate of the rolling granulator was set to 490 rpm, thereby regulating the centrifugal acceleration to 31 G, and the same evaluations as in Example 5 were attempted. The catalyst B4 is liable to generate scattering from the rolling granulator during the preparation work, and judging that a possibility that the reproducibility of the supporting amount by a preparation lot is deteriorated becomes high, the subsequent steps and the strength measurement and oxidation reaction test were not carried out.

Example 10

In 10,000 ml of distilled water at room temperature, 1,000 g of molybdenum trioxide, 96.09 g of an 85% by weight phosphoric acid aqueous solution, 37.91 g of vanadium pentoxide, 65.73 g of a 60% by weight arsenic acid aqueous solution, and 22.1 g of cupric oxide were charged, the temperature was increased to 95° C. while agitating, and the contents were dissolved while heating and refluxing at 95° C. over 10 hours, thereby obtaining a reddish brown solution. This solution was spray dried to obtain a catalytic active component solid. A formulation of the catalytic active component solid as determined from the charged amounts of the raw materials is $Mo_{10}V_{0.6}P_{1.1}Cu_{0.4}As_{0.4}$.

500 parts of a spherical porous alumina carrier having a diameter of 3.5 mm was charged into a rolling granulator having a diameter of a bottom plate of 23 cm. By rotating the bottom plate at 100 rpm, the centrifugal acceleration was set to 1.3 G. 430 parts of the catalytic active component solid and 70 parts of a strength improver (glass fiber) were uniformly mixed and subjected to coating and shaping with about 60 parts of an 80% by mass ethanol aqueous solution as a liquid binder by a rolling granulation method. Subsequently, the resulting shaped product was calcined under air circulation at 310° C. over 5 hours, thereby obtaining a desired coated catalyst A10. The catalyst A10 was subjected to the same evaluations as in Example 5.

The oxidation reaction results and the strength measurement results of the catalyst A10 are shown in Table 2.

Example 11

A catalyst A11 was prepared in the same method as in Example 10, except that in Example 10, the revolution rate of the bottom plate of the rolling granulator was set to 260 rpm, thereby regulating the centrifugal acceleration to 8.7 G, and the same evaluations as in Example were carried out. The oxidation reaction results and the strength measurement results of the catalyst A11 are shown in Table 2.

TABLE 2

| Catalyst name | Relative centrifugal acceleration (G) | Attrition resistance (%) | Methacrolein conversion (mol %) | Methacrylic acid yield (mol %) |
|---|---|---|---|---|
| A5 | 0.72 | 0.69 | 92.1 | 76.0 |
| A6 | 3.3 | 0.55 | 94.5 | 75.2 |
| A7 | 5.1 | 0.58 | 94.6 | 76.2 |
| A8 | 10 | 0.67 | 94.0 | 74.8 |
| A9 | 21 | 0.31 | 93.3 | 76.2 |
| A10 | 1.3 | 0.27 | 83.1 | 66.8 |
| A11 | 8.7 | 0.34 | 83.7 | 67.1 |
| B3 | 0.32 | 2.21 | 89.9 | 76.1 |
| B4 | 31 | Not carried out | Not carried out | Not carried out |

While the invention has been described in detail and with reference to specific embodiments thereof, it will be apparent to one skilled in the art that various changes and modifications can be made therein without departing from the spirit and scope thereof.

It is to be noted that the present application is based on a Japanese patent application filed on Oct. 10, 2013 (Japanese Patent Application No. 2013-212622), and the contents are incorporated herein by reference. In addition, all the references cited herein are incorporated as a whole.

INDUSTRIAL APPLICABILITY

The present invention is useful in industrial plants of producing unsaturated carboxylic acids.

The invention claimed is:

1. A method for producing acrylic acid, comprising:
partially oxidizing acrolein in the presence of molecular oxygen and
using a supported catalyst obtained by feeding a liquid binder component and a catalytic active component containing molybdenum and vanadium and/or a precursor thereof into a rolling granulator and conducting granulation at a relative centrifugal acceleration of 0.5 G to 30 G, said obtained catalyst having a formulation of a composite metal oxide represented by the following formula (1):

$$(Mo)_{12}(V)_a(W)_b(Cu)_c(Sb)_d(X)_e(Y)_f(Z)_g(a)_h \quad (1)$$

wherein Mo, V, W, Cu, Sb and O represent molybdenum, vanadium, tungsten, copper, antimony and oxygen, respectively; X represents at least one element selected from the group consisting of an alkali metal and thallium; Y represents at least one element selected from the group consisting of magnesium, calcium, strontium, barium and zinc; Z represents at least one element selected from the group consisting of niobium, cerium, tin, chromium, manganese, iron, cobalt, samarium, germanium, titanium and arsenic; and a, b, c, d, e, f, g, and h represent atomic ratios of the respective elements, in which a is (0<a≤10), b is (0≤b≤10), c is (0<c≤6), d is (0≤d≤10), e is (0≤e≤0.5), f is (0≤f≤1) and g is (0≤g<6) relative to 12 of the molybdenum atom, and h is a number of oxygen atoms necessary for satisfying valences of the above-described respective components.

2. A supported catalyst, which is obtained by feeding a liquid binder component and a catalytic active component containing molybdenum and vanadium and/or a precursor thereof into a rolling granulator and conducting granulation at a relative centrifugal acceleration of 0.5 G to 30 G.

3. The supported catalyst according to claim 2, wherein the catalytic active component and/or the precursor thereof contains molybdenum, vanadium and copper.

4. The supported catalyst according to claim 2, wherein the catalytic active component and/or the precursor thereof contains molybdenum, vanadium and phosphorus.

5. A method for producing methacrylic acid comprising:
partially oxidizing methacrolein in the presence of molecular oxygen and
using a supported catalyst obtained by feeding a liquid binder component and a catalytic active component containing molybdenum and vanadium and/or a precursor thereof into a rolling granulator and conducting granulation at a relative centrifugal acceleration of 0.5 G to 30 G, said obtained catalyst having a formulation of a composite metal oxide represented by the following formula (3):

$$(Mo)_{10}V_aP_b(NH_4)_c(X)_d(Y)_e(Z)_g(O)_f \qquad (3)$$

wherein Mo represents molybdenum; V represents vanadium; P represents phosphorus; (NH$_4$) represents an ammonium group; X represents at least one element selected from the group consisting of K, Rb and Cs; Y represents at least one element selected from the group consisting of Sb, As, Cu, Ag, Mg, Zn, Al, B, Ge, Sn, Pb, Ti, Zr, Cr, Re, Bi, W, Fe, Co, Ni, Ce and Th; and a to e represent atomic ratios of the respective elements, in which a is (0.1≤a≤6.0), b is (0.5≤b≤6.0), c is (0≤c≤10.0), d is (0≤d≤3.0), e is (0≤e≤3), and f is a numerical value determined by oxidized states of the respective elements other than O and atomic ratios thereof.

6. The method of claim 5, wherein a is (0.3≤a≤2.0), b is (0.7≤b≤2.0), c is (0≤c≤5), d is (0≤d≤1.5), and e is (0.01≤e≤0.5).

* * * * *